United States Patent [19]

Tusé et al.

[11] Patent Number: 5,385,832

[45] Date of Patent: Jan. 31, 1995

[54] METHOD FOR OBTAINING HIGHLY PURE BETA 1,3-GLUCAN FROM EUGLENA

[75] Inventors: Daniel Tusé, Fremont; Leticia Márquez, Berkeley; Leslie A. Hokama, Mountain View, all of Calif.

[73] Assignee: SRI International, Menlo Park, Calif.

[21] Appl. No.: 34,609

[22] Filed: Mar. 22, 1993

Related U.S. Application Data

[63] Continuation of Ser. No. 802,323, Dec. 4, 1991, abandoned, which is a continuation of Ser. No. 332,502, Mar. 31, 1989, Pat. No. 5,084,386.

[51] Int. Cl.$^6$ ............... C12P 19/04; D06M 16/00; A01G 7/00
[52] U.S. Cl. ............... 435/101; 435/257.1; 435/257.4; 435/262; 435/946; 47/1.4
[58] Field of Search ............ 435/101, 946, 262, 257.1, 435/257.4; 47/1.4

[56] References Cited

U.S. PATENT DOCUMENTS 4,745,058  5/1988  Townsley ..................... 435/101

FOREIGN PATENT DOCUMENTS 0322393  6/1989  European Pat. Off. .

OTHER PUBLICATIONS

*Patent Abstracts of Japan* entitled "Production of β-1,-3-glucan" (24 May 1989) vol. 13, No. 224, (C-599) [3572] & Japanese Patent Application No. 137297 (7 Feb. 1989).
Patent Abstracts of Japan entitled "Production of β-1,-3-glucan by cell of genus Euglena" (15 Aug. 1988) vol. 12, No. 299, (C-520) [3146] & Japanese Patent Application No. 6371192 (31 Mar. 1988).
Patent Abstracts of Japan entitled "Culturing of single-celled green algae" (18 Jul. 1981) vol. 5, No. 111, (C-63) [783] & Japanese Patent Application No. 5648883 (2 May 1981).
Di Luzio, "Immunopharmacology of glucan: a broad spectrum enhancer of host defense mechanisms" *Trends in Pharmaceutical Science* (1983) 4:344–347.
Tomos et al., "A protein-glucan intermediate during paramylon synthesis" *Biochem. J.* (1978) 174:283–290.
Wolken et al., "Euglena: an experimental organism for biochemical and biophysical studies" Institute of Microbiology, Rutgers, The State University, (1961) pp. 13.
Dwyer et al. (1971) *Aust. J. Biol. Sci.* 24:15–22.
Prasada et al. (1984) *Phytochemistry* 23:2531–2534.
Kiss et al., (1986) *J. of Phycology* 22:327–333.
Invi et al. (1988) *Agric Biol Chem* 52:49–54.

*Primary Examiner*—David M. Naff
*Assistant Examiner*—L. Blaine Lankford
*Attorney, Agent, or Firm*—Morrison & Foerster

[57] ABSTRACT

Substantially pure, pyrogen-free beta-1,3-glucan is produced by cultivating Euglena cells in a defined growth medium and under specified conditions that provide a cell mass comprising 70% to 90% beta-1,3-glucan on a dry weight basis, separating the cell mass from the supernatant, extracting the cell mass with methanol and chloroform, acid-washing the extracted cell mass, and washing the acid-treated material with water.

3 Claims, 3 Drawing Sheets

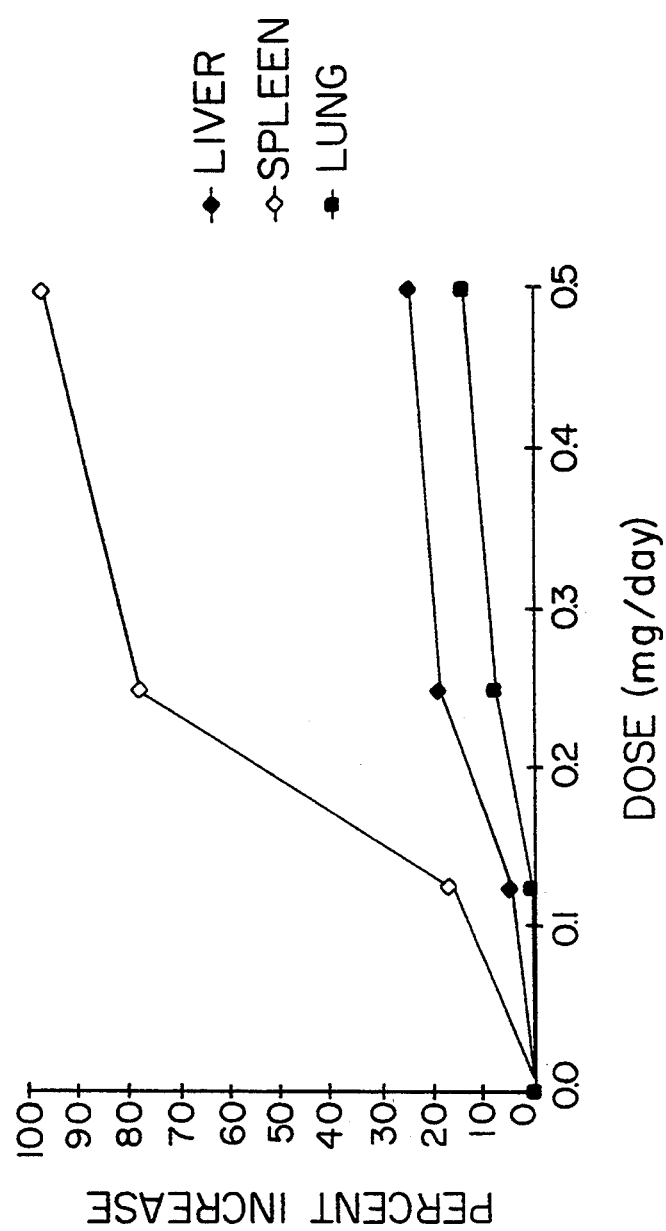

METHOD FOR OBTAINING HIGHLY PURE BETA 1,3-GLUCAN FROM EUGLENA

This application is a continuation of application Ser. No. 07/802,323, filed Dec. 4, 1991, now abandoned, which is a continuation of application Ser. No. 07/332,502, filed Mar. 31, 1989, now U.S. Pat. No. 5,084,386.

DESCRIPTION

Technical Field

This invention relates to method for producing beta-1,3-linked polyglucose in Euglena. This biopolymer, also called beta-1,3-glucan or paramylon, is useful in a number of different applications, including in medicine as an immunostimulant or immunopotentiator, in cosmetics as a bioactive ingredient for wrinkle treatment, or as a foodstuff.

Background

Beta-1,3-glucan is known as a nonspecific immunostimulator. Specifically, it has been shown to be a potent macrophage activator. Such activation induces a range of effects, including increased resistance to infectious agents and tumors, enhanced cytokine production, and accelerated wound healing.

Although a number of microorganisms are known to produce beta-1,3-glucan, including algae of the genus Euglena, it is generally produced in *Saccharomyces cerevisiae* (baker's yeast) and is extracted from the cell wall by a complicated process that chemically degrades the glucan. Optimized yields of beta-1,3-glucan from yeast range from only 5% to 7% of the cellular mass. Besides the low yield, the destructive nature of the extraction process gives a heterogeneous product. This heterogeneity makes quality control difficult and has resulted in problems with the reproducibility of immune stimulation studies carried out with the yeast-produced beta-1,3-glucan.

The present invention is based on the inventors' investigation of Euglena as a source of beta-1,3-glucan and the finding that under certain conditions the glucan is produced at much higher yield than in yeast and can be purified via a considerably simpler process that produces a more homogeneous product.

DESCRIPTION OF THE INVENTION

One aspect of the invention is a process for producing beta-1,3-glucan comprising cultivating Euglena cells in the dark in a growth medium that initially contains sufficient carbon source to provide an initial carbon concentration of about 4 to about 16 g/L and sufficient nitrogen source to provide a molar ratio of carbon to nitrogen in the range of about 10 to 40 and is maintained at a temperature of about 25° C. to about 30° C., a pH of about 2 to about 5, and a dissolved oxygen concentration of about 4 to 40 ppm.

During growth under these conditions, the cells accumulate the beta-1,3-glucan intracellularly in a relatively pure, nearly crystalline form. At the end of the cultivation, the beta-1,3-glucan constitutes about 70% to 90% of the dry weight of the cell mass. This high yield and relative in vivo purity facilitates purifying the beta-1,3-glucan without degrading it.

Thus, another aspect of the invention is a process for obtaining substantially pure, essentially pyrogen-free beta-1,3-glucan from a culture of Euglena cells in which the cell mass comprises about 70% to about 90% beta-1,3-glucan on a dry weight basis comprising carrying out the following steps under aseptic conditions:

(a) separating the cells from the culture supernatant;

(b) disrupting the cells and extracting the cells with an extractant that removes lipid and pigment from the cellular mass;

(c) separating the extracted cellular mass from the extractant;

(d) heating the extracted cellular mass with agitation in a dilute acid wash to separate cellular debris from the beta-1,3-glucan;

(e) separating the acid-washed beta-1,3-glucan from the acid wash; and (f) washing the product of (e) with pyrogen-free sterile water to produce said substantially pure, essentially pyrogen-free beta-1,3-glucan.

BRIEF DESCRIPTION OF THE DRAWINGS

FIGS. 1, 2(a)–(c), and 3 are graphs of the results of the bioassays described in the Examples, infra.

MODES FOR CARRYING OUT THE INVENTION

Euglena

Figure 2A:
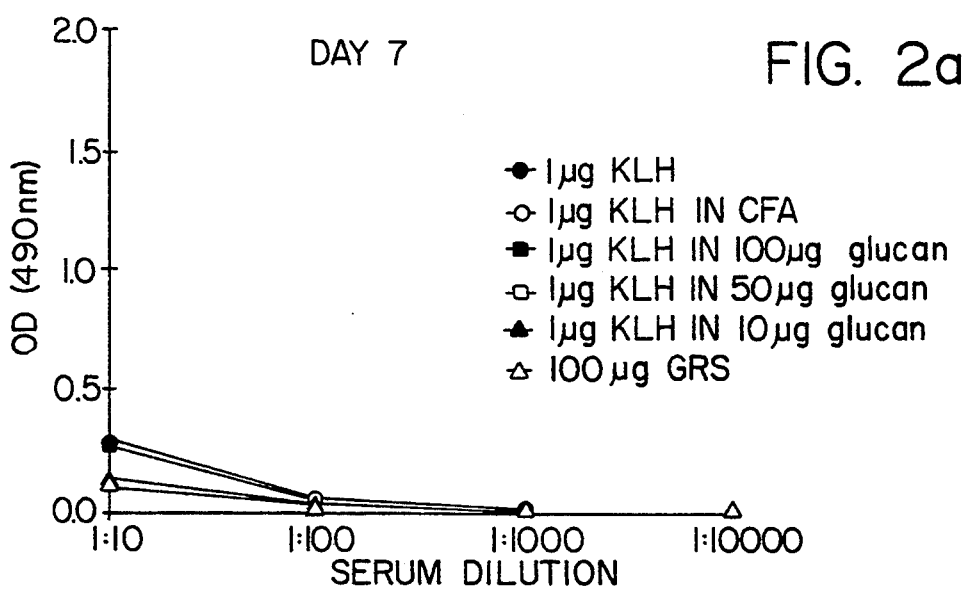

Any species of the genus Euglena may be used in the process. Examples are *Euglena gracilis, Euglena intermedia, Euglena piride,* and other Euglenoids, for example *Astasia longa. Euglena gracilis* strain z, (available through the American Type Culture Collection) is preferred. The cells are normally added to the medium at about $10^5$–$10^6$ cells/mi.

Culture Medium

The culture medium is basically comprised of (1) a carbon source, (2) a nitrogen source, (3) macronutrients required for cell growth, (4) trace elements required by or desirable for cell growth, and (5) vitamins that promote cell growth. Examples of carbon sources are: simple sugars such as glucose, fructose, and maltose; oligosaccharides; complex carbohydrates such as cornstarch; alkanoic and fatty acids; and lower alkanols, i.e., 1–6 carbon atoms. The concentration of carbon source in the medium should be sufficient to provide an initial carbon content of 4 to 16 g/L, preferably 8 to 12 g/L. Typical nitrogen sources include ammonium salts such as ammonium phosphate and ammonium sulfate, and amino acids. The nitrogen source should be present in the medium in an amount sufficient to provide an initial molar ratio of carbon to nitrogen in the range of 10–40, preferably 25 to 35. Macronutrients include essential elements/ions such as phosphorus, sulfur, $Mg^{+2}$ (i.e., $MgSO_4$, $MgCO_3$, $MgCl_2$), $Ca^{+2}$ ($CaSO_4$, $CaCO_3$), $K^+$ ($KH_2PO_4$) and $Na^+$ ($Na_2SO_4$, $Na_2$-EDTA. Desirable trace elements that promote cell growth include Zn, Mn, Mo, Cu, V, Co, Ni, B and Fe. These elements may be incorporated into the culture medium in the form of water-soluble salts. Preferred vitamins to be added to the medium are thiamine and $B_{12}$.

Culture Conditions

The pH of the medium should be kept acidic, i.e., normally in the range of 2 to 6 and preferably 3–4.5. The pH may be maintained within these limits by addition of base (e.g., NaOH, KOH, $Ca(OH)_2$) as appropriate. The temperature is normally kept in the range of 25° C. to 30° C., preferably 25° C. to 27° C.. The cultivation is carried out in the dark since illumination promotes photosynthesis and favors production of protein over beta-1,3-glucan.

The culture medium is agitated during the growth cycle to promote aeration of the medium. Stirring or other means may be used for this purpose. The oxygen concentration of the medium may vary between ambient concentration or slightly less (about 4–8 ppm) to about 40 ppm. In order to achieve concentrations above ambient, the aerating gas must be enriched in $O_2$.

Cells will typically be harvested after about 3–4 days of incubation under the above conditions.

Purification of Beta-1,3-glucan

The purification of the glucan from the cells should be conducted under aseptic conditions.

The cells are first separated from the culture supernatant by sedimentation, centrifugation or other conventional means. The cells may be washed, if desired, with water prior to the extraction. The cells are then disrupted either by sonication or treatment with a solvent that disrupts the cell wall. Preferably the cells are extracted with methanol and chloroform that both lyses the cell membrane and extracts lipids and pigment from the cell mass. The extraction is preferably carried out with mixing and may be repeated, if necessary, to achieve more effective extraction. After the extraction, the depigmented cell mass is washed with a dilute mineral acid solution such as HCl or $H_2SO_4$ to break the rest of the cell debris away from the crystalline glucan and remove pyrogens. The acid wash is carried out with heating, preferably at approximately 100° C., with agitation.

Following the acid wash, the glucan is washed repeatedly with pyrogen-free water to remove residual pigment. The resulting product is a white crystalline material of at least about 95–97% purity containing less than about 0.08 endotoxin units per milliliter.

Formulation and Use

The crystalline beta-1,3-glucan may be formulated as such or solubilized such as by physical, chemical and enzymatic methods that reduce the size of the polymer chains. For parenteral administration (e.g., iv, im, ip, etc.) the glucan is suspended or dissolved in conventional parenteral vehicles such as physiological saline, dextrose solution, or the like. The concentration of glucan in the formulation will normally be in the range of 0.01 to 1.0% by weight. Modifications in concentration may be necessary depending upon the type of application. For use in other medical indications, e.g., to facilitate wound healing, it may be desirable to formulate the glucan for topical administration in the form of a cream, lotion, gel or the like. Again, conventional pharmaceutically acceptable carriers may be used in preparing such formulations.

The medical use of glucan has been extensively reviewed in the art. See, for instance, "Immunopharmacology of Glucan", N. R. DiLuzio, *Trends in Pharmacological Sciences,* (August 1983), Vol. 4, pp. 344–347. Specific formulations and dosages for specific indications may be found in such literature.

EXAMPLES

The following examples illustrate the cultivation of *Euglena gracilis* to produce beta-1,3-glucan, the purification of beta-1,3-glucan from the Euglena cells, and the biological activities of that beta-1,3-glucan. These examples are offered by way of illustration and are not intended to limit the invention in any manner.

Cultivation of *Euglena gracilus*

*Euglena gracilis* strain z was used. This strain is available from the American Type Culture Collection, No. E12716. A 100 ml inoculum of this strain was prepared from a culture grown in the dark at 25°–27° C., pH 3.5–4.0, with mixing (120–200 rpm) for 72 hours.

A growth medium having the following composition was employed.

| Ingredient | Concentration (g/L) |
| --- | --- |
| Glucose | 10–40 |
| $(NH_4)_2SO_4$ | 1.9 |
| $KH_2PO_4$ | 0.25 |
| $MgCO_3$ | 0.60 |
| $CaCO_3$ | 0.12 |
| $Na_2$ EDTA | 0.05 |
| $FeSO_4(NH_4)_2SO_4.6H_2O$ | 0.05 |
| $MnSO_4.H_2O$ | 0.018 |
| $ZnSO_4.7H_2O$ | 0.025 |
| $(NH_4)_6Mo_7O_{24}.4H_2O$ | 0.004 |
| $CuSO_4$ | 0.0012 |
| $NH_4VO_3$ | 0.0005 |
| $CoSO_4.7H_2O$ | 0.0005 |
| $H_3BO_3$ | 0.0006 |
| $NiSO_4.6H_2O$ | 0.0005 |
| Vitamin $B_1$ (HCl) Thiamine HCl | 0.0025 |
| Vitamin $B_{12}$ CN Cyanocobalmin | 0.000005 |

100 ml inoculum was added to 1 liter of medium in a flask fitted with a stirrer and an aerator. The culture was maintained in the dark at 25°–27° C. for 72–96 hr. pH was kept at 3.0–4.5 and adjusted with NaOH as necessary. Stirring was maintained at about 175 rpm (120–200 rpm range). The culture was aerated with air and/or pure oxygen at an average flow rate of 1 L/min (0.5–2.3 L/min range) to provide a dissolved $O_2$ concentration of 8 to 40 ppm.

Euglena can be grown in other types of fermentors affording aseptic control and efficient mass transfer of gasses and nutrients. These systems include, but are not limited to, chemostats, stirred tank reactors, airlift reactors and perfusion systems.

Purification

All purification procedures were conducted under aseptic conditions.

Cells were harvested by centrifuging the culture at 3000–4000 rpm for 5–10 min. The cell mass was then washed with pyrogen-free water and recentrifuged. Optionally, the cells may be sonicated to disrupt the cell wall. The water-washed solids were then placed in a flask equipped with a stirrer and an equal volume (up to 3×vol.) of methanol was added. The mixture was refluxed at 65° C. for 5–10 min with stirring and then allowed to cool. Two volumes of chloroform were then added and the mixture was stirred an additional 20–30 min at ambient temperature. The cell mass was then vacuum-filtered and washed with 2–3 additional volumes of chloroform. The filtered cell mass was transferred to a flask and an equal volume of methanol and twice the volume of chloroform were added. This mixture was stirred at ambient temperature for 30–60 min and then vacuum filtered as above.

The filtered mass was then taken up in a sufficient volume of 1N HCl to provide a relatively dilute suspension. This mixture was boiled until no solvent odor was detectable followed by refluxing for an additional two hours. The solids were then centrifuged and washed repeatedly with water to provide substantially pure beta-1,3-glucan in the form of a white crystalline solid. This material was stored at 4° C. pending use.

Bioactivity

Various tests were carried out to characterize the bioactivity of the beta-1,3-glucan prepared from Euglena. These assays are described below.

Hepatosplenomegaly assay. Forty 6- to 8-week-old black mice (C57BL/6) each weighing 18 to 20 g were divided into four groups. The 10 control mice were injected intravenously with physiological saline while the remaining experimental mice were given varying doses of particulate beta-1,3-glucan (0.5, 0.25 and 0.125 mg/day) in physiological saline. Doses were administered on days 1, 2 and 3. On day 1 the beta-1,3-glucan was given in two equal doses at least an hour apart because of the demonstrated sensitivity of the mice to the glucan; only one injection, the entire dose, was given on days 2 and 3. On day 6, the mice were sacrificed and the reticuloendothelial system (RES) organs removed—the spleen, liver and lungs. Each organ was weighed individually and the average weight and standard deviations calculated and are tabulated below. Utilizing these data, the dose response curve shown in FIG. 1 was generated. As shown the glucan-treated animals demonstrated a considerable increase in the weight of their RES organs as compared to the control animals. This increase indicates significant stimulation of the immune system of the treated animals.

TABLE 1

BIOACTIVITY ASSAY
MOUSE HEPATOSPLENOMEGALY TEST FOLLOWING IV
ADMINISTRATION OF PARTICULATE GRS-1

| Group (n = 10) | Average Spleen Weight (g) | Standard Deviation | Percent Increase[a] | Average Liver Weight (g) | Standard Deviation | Percent Increase | Average Lung Weight (g) | Standard Deviation | Percent Increase |
|---|---|---|---|---|---|---|---|---|---|
| Control | 0.062 | 0.0073 | — | 1.225 | 0.0840 | — | 0.144 | 0.0122 | — |
| 0.5 mg/day | 0.123[c] | 0.0176 | 96.9 | 1.516[c] | 0.1302 | 23.8 | 0.165[b] | 0.0222 | 14.6 |
| 0.25 mg/day | 0.111[c] | 0.1822 | 78.0 | 1.444[b] | 0.0754 | 17.9 | 0.155 | 0.0112 | 7.6 |
| 0.125 mg/day | 0.073 | 0.1592 | 16.2 | 1.276 | 0.0968 | 4.2 | 0.145 | 0.0088 | 0.7 |

[a]Percent increase was determined by the following equation:

$$\text{Percent increase} = \frac{\text{Average weight (g) experimental organ} - \text{Average weight (g) control organ}}{\text{Average weight (g) of control organ}} \times 100$$

[b]$p < 0.01$
[c]$p < 0.001$

Bacterial challenge. The bacterial challenge assay was conducted to determine the effects of beta-1,3-glucan on the susceptibility of mice to *Listeria monocytogenes*. Three concentrations of beta-1,3-glucan suspended in 0.5 ml pyrogen-free saline were administered intravenously on days 1, 2, and 3, and the mice were then challenged intraperitoneally on day 6 with $6.0 \times 10^6$ *L. monocytogenes*. This assay was repeated many times with differing concentrations of the pathogen. The results tabulated below are representative. The results indicate that the beta-1,3-glucan at 3 doses of 0.5 mg per animal significantly increased the number of survivors exposed to Listeria organisms. Avicel ® (FMC Corp.), a cellulosic particulate material of similar size to beta-1,3-glucan, did not protect mice from a Listeria challenge, indicating that beta-1,3-glucan elicits a biological response independent of its particulate nature.

TABLE 2

EFFECT OF BETA-1,3-GLUCAN TREATMENTS
ON THE SUSCEPTIBILITY OF C57BL/6 MICE
TO *LISTERIA MONOCYTOGENES* CHALLENGE

| Dose of beta-1,3-glucan | No. Survivors/No. Total | Significance |
|---|---|---|
| 0.50 mg | 7/10 | $p < .005$ |
| 0.25 mg | 3/10 | n.s. |
| 0.50 mg Avicel | 0/10 | n.s. |
| Saline | 0/10 | — |

Toxicity test. Solutions of the native particulate beta-1,3-glucan were administered intraperitoneally to mice in a single dose of either 50, 500, or 5000 mg/kg or administered in doses of 15, 150, or 1500 mg/kg on 8 consecutive days. All mice survived and showed no significant signs of ill health, indicating that the levels administered were not toxic. On day 10, necropsy was performed to determine the effects of the beta-1,3-glucan. Some visceral adhesion was found, but this was probably due to the extremely high doses administered of this recalcitrant particulate material. The lack of significant toxicity of beta-1,3-glucan suggests its potentially high therapeutic index.

Tumor challenge assay. The effect of beta-1,3-glucan on the survival time of mice challenged with B16 melanoma was evaluated using short-term (Table 3 below) or long-term (Table 4 below) treatment schedules. As reported, there was a consistently significant increase in survival time in animals treated with 0.5 mg beta-1,3-glucan. More variable responses were seen with lower doses of particulate beta-1,3-glucan. In other experiments where beta-1,3-glucan treatments were delayed until day 7, no significant therapeutic effect was observed.

TABLE 3

EFFECT OF BETA-1,3-GLUCAN TREATMENTS
ON THE SURVIVAL OF C57BL/6 MICE
INOCULATED WITH B16 MELANOMA CELLS

| Treatment[a] (beta-1,3-glucan dose) | Mean Survival Time (Days) | Percent Increase | Significance[b] |
|---|---|---|---|
| Saline | 24.2 ± 4.96 | — | — |
| 0.125 mg | 33.5 ± 10.21 | 38 | $p < .02$ |
| 0.250 mg | 34.3 ± 10.55 | 42 | $p < .01$ |
| 0.500 mg | 38.4 ± 7.85 | 59 | $p < .001$ |

[a]Ten mice per group were injected subcutaneously on day 0 with $1 \times 10^5$ B16 melanoma cells on the rear flank. Each group received its respective beta-1,3-glucan or saline treatment on days 1, 4, 7, 10 and 13 by intravenous injection in 0.5 ml pyrogen-free saline.
[b]Statistical significance was determined by a student's t-test of the mean survival time for each group as compared with the saline control.

TABLE 4
EFFECT OF BETA-1,3-GLUCAN TREATMENTS ON THE SURVIVAL OF C57BL/6 MICE INOCULATED WITH B16 MELANOMA CELLS

| Treatment[a] | Mean Survival Time (Days) | Percent Increase | Significance[b] |
|---|---|---|---|
| Saline | 29.7 ± 5.15 | — | — |
| 0.25 mg beta-1,3-glucan | 30.0 ± 9.76 | 1 | n.s. |
| 0.50 mg beta-1,3-glucan | 35.0 ± 4.74 | 18 | $p < .05$ |

[a]Ten mice per group were injected subcutaneously on day 0 with $1 \times 10^5$ B16 melanoma cells on the rear flank. Each group received its respective beta-1,3-glucan or saline treatment on days 1, 4, 7, 10, 13, 16, 19, 22, 25 and 28 by intravenous injection in 0.5 ml pyrogen-free saline.

[b]Statistical significance was determined by a Student's t-test of the mean survival time for each group as compared with the saline control.

Antibody production to beta-1,3-glucan. Serum from pre- and post-beta-1,3-glucan-treated rabbits was collected and assayed to determine whether any antibodies to beta-1,3-glucan were produced. Two different preparations of beta-1,3-glucan were tested by ELISA, and results indicate that beta-1,3-glucan, prepared and purified as above, does not elicit an antigen response.

Figure 2B:
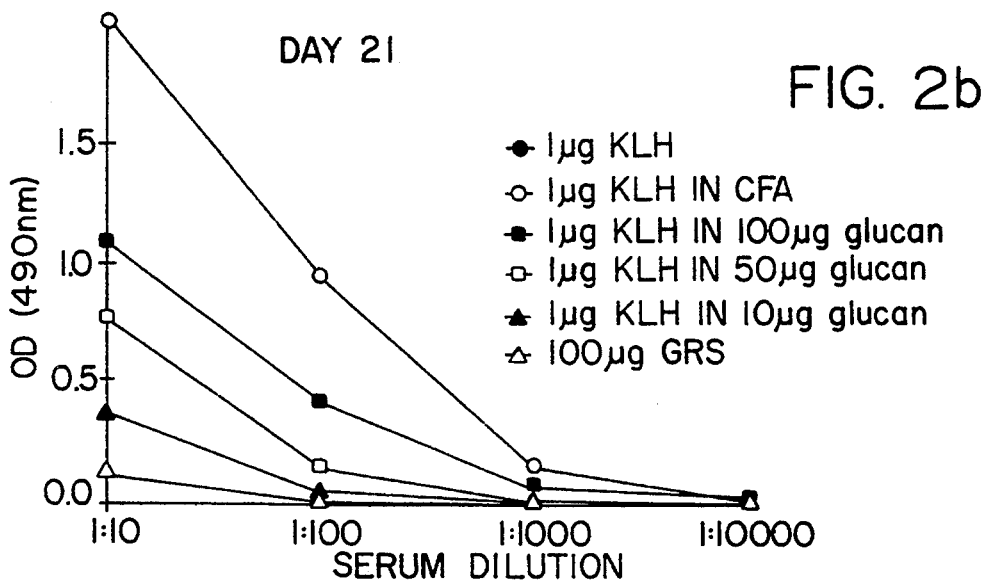
Figure 2C:
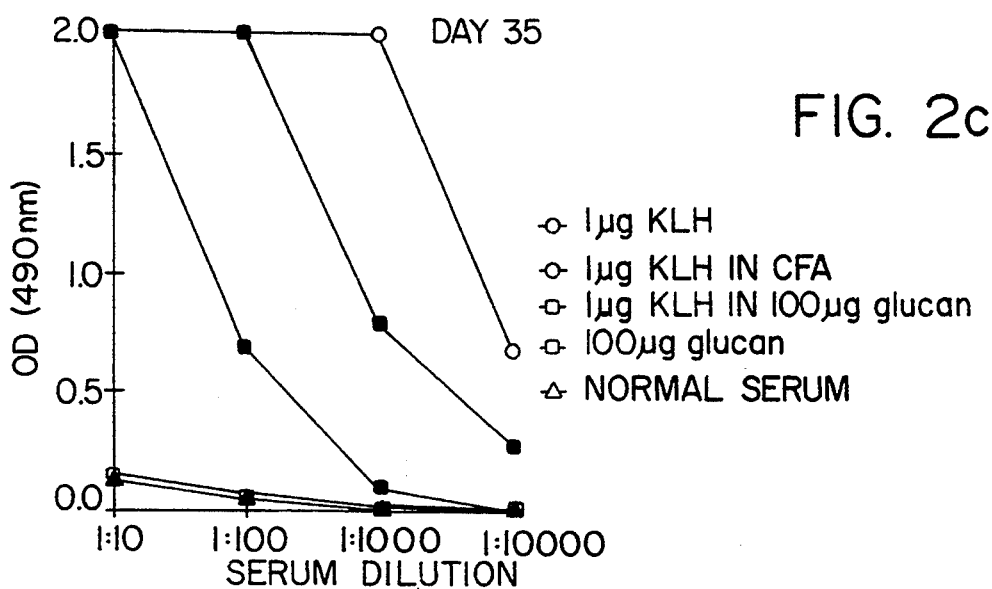

Adjuvant activity. The ability of beta-1,3-glucan to assist in the generation and potentiation of humoral immune responses was evaluated by immunizing mice with keyhole limpet hemocyanin (KLH) mixed with various concentrations of beta-1,3-glucan. Controls consisted of saline and complete Freund's adjuvant (CFA). At 7, 21, and 35 days after immunization, serum was collected from these animals. The animals were boosted on day 21 with KLH in saline, and serum samples were again collected on day 42. On day 7 results show that antibody production to KLH, as measured by ELISA, was enhanced approximately 5-fold in the animals treated with CFA or 100 ug beta-1,3-glucan (see FIG. 2a) as compared with animals treated with KLH in saline. On day 21, the 100 ug beta-1,3-glucan-treated mice showed a 10-fold greater level of antibody production than mice treated with KLH alone (see FIG. 2b). After boosting the remaining mice with 1 ug KLH on day 21, the serum was collected 14 days later and tested. The levels of antibodies to KLH were very high in all groups, however the mice treated with beta-1,3-glucan demonstrated significantly higher antibody titers (approximately 10-fold) than mice immunized with KLH alone (see FIG. 2c).

Figure 3:
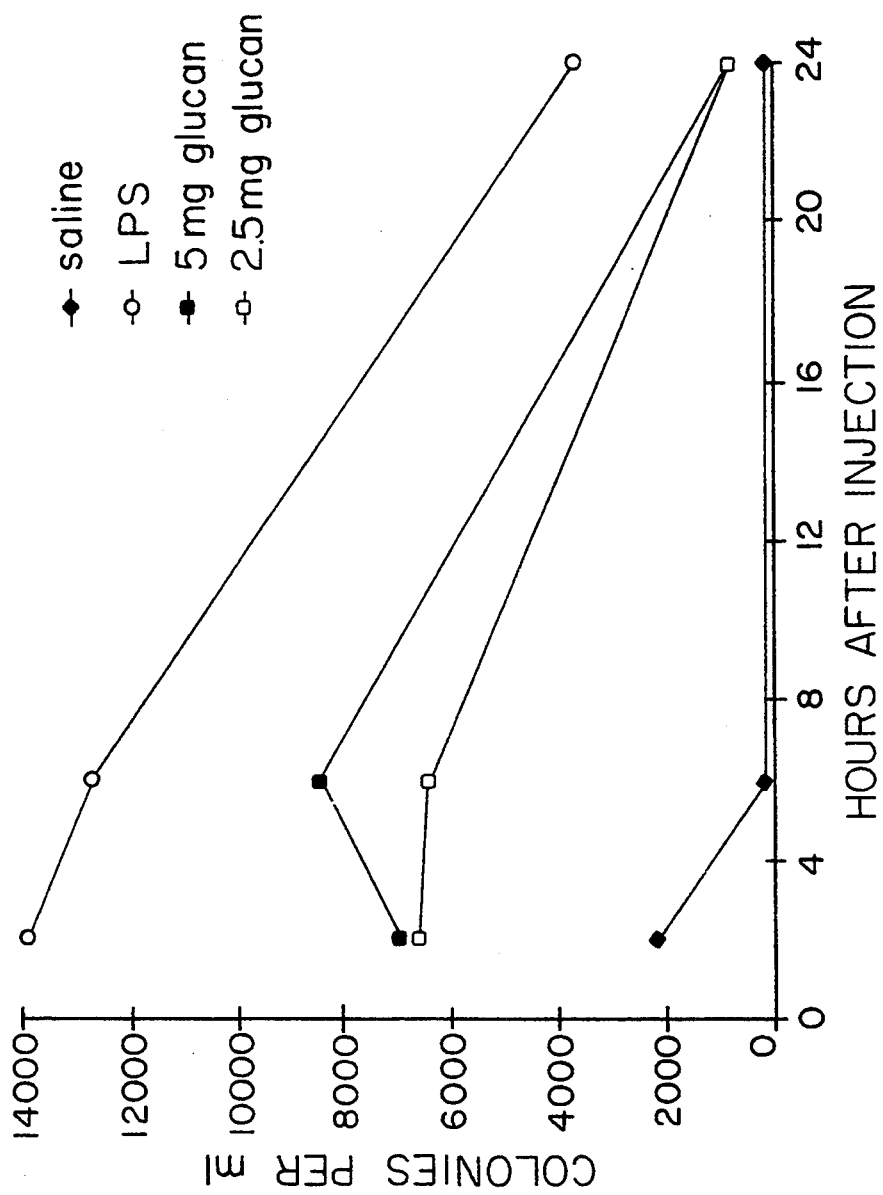

Colony-stimulating activity. Preliminary experiments examining the ability of beta-1,3-glucan to induce the release of bone marrow colony-stimulating activity (CSA) were performed. C57BL/6 mice were injected intravenously with various concentrations of beta-1,3-glucan, and serum samples were collected from groups of three mice at various times after injection and subsequently assayed for CSA. In this assay, normal mouse bone marrow cells were cultured in the presence of various dilutions of each serum sample in a soft-agar medium. Seven days later, the number of cell colonies arising in these cultures was determined for each serum dilution, and the results expressed as the number of bone marrow colonies stimulated by 1 ml of each serum. As seen in FIG. 3, administration of 2.5 or 5 mg of particulate beta-1,3-glucan induced the release of significant amounts of serum beta-1,3-glucan. Bacterial lipopolysaccharide (LPS), a well-known potent stimulator of CSA in animals, was included in this study as a positive control and also demonstrated the ability to induce serum CSA. These results also suggest that beta-1,3-glucan stimulated the release of CSA in a dose-dependent manner. These data are consistent with serum CSA studies of others using particulate yeast glucan, and they suggest that Euglena-produced beta-1,3-glucan can be effective in stimulating the recovery of bone marrow depleted by irradiation or chemotherapy.

Modifications of the above-described modes for carrying out the invention that are obvious to those of skill in the fields of microbiology, biochemistry, immunology and related fields are intended to be within the scope of the following claims.

We claim:

1. A process for obtaining substantially pure beta-1,3-glucan from a culture of Euglena cells in which the cells comprise about 70% to 90% beta-1,3-glucan on a dry weight basis comprising carrying out the following steps under aseptic conditions:
    (a) separating the cells from the culture;
    (b) lysing the cells and extracting the cells with an extractant that removes lipid and pigment from the cells and obtaining crystalline beta-1,3-glucan;
    (c) separating the crystalline beta-1,3-glucan from the extractant;
    (d) adding acid to the crystalline beta-1,3-glucan with heating and agitation to form an acid soluble and an acid insoluble portion, said acid insoluble portion containing the crystalline beta-1,3-glucan; and
    (e) washing the acid insoluble portion containing the crystalline beta-1,3-glucan with sterile water to produce said substantially pure beta-1,3-glucan of at least about 95% purity containing less than about 0.08 endotoxin units per milliliter.

2. The process of claim 1 wherein the extractant comprises methanol and chloroform.

3. The process of claim 1 wherein the acid is dilute HCl.

* * * * *